United States Patent [19]

Sakai et al.

[11] Patent Number: 4,892,939

[45] Date of Patent: Jan. 9, 1990

[54] OLIGOPEPTIDYL-5-FLUOROURIDINE COMPOUNDS AND PROCESS FOR PREPARING THE SAME

[75] Inventors: Katsumi Sakai, Tokyo; Kiyoaki Chou; Takeshi Endo, both of Nakaniikawa, all of Japan

[73] Assignee: Fuji Kagaku Kogyo Kabushiki Kaisha, Toyama, Japan

[21] Appl. No.: 148,507

[22] PCT Filed: May 30, 1986

[86] PCT No.: PCT/JP86/00278

§ 371 Date: Jan. 29, 1988

§ 102(e) Date: Jan. 29, 1988

[87] PCT Pub. No.: WO87/07276

PCT Pub. Date: Dec. 3, 1987

[51] Int. Cl.$^4$ .................................. C07H 19/06
[52] U.S. Cl. ........................ 536/23; 530/331
[58] Field of Search ................ 536/23; 530/33

[56] References Cited

U.S. PATENT DOCUMENTS 3,975,367  8/1976  Gish et al. ............................. 536/23
4,340,728  7/1982  Endo et al.

FOREIGN PATENT DOCUMENTS 56-77298  6/1981  Japan.
57-91994  6/1982  Japan.
57-91996  6/1982  Japan.
57-91997  6/1982  Japan.
57-91998  6/1982  Japan.
1134397  6/1986  Japan ..................... 514/50

*Primary Examiner*—John W. Rollins
*Attorney, Agent, or Firm*—Birch, Stewart, Kolasch & Birch

[57] ABSTRACT

New 5-fluorouridine compounds of the general formula:

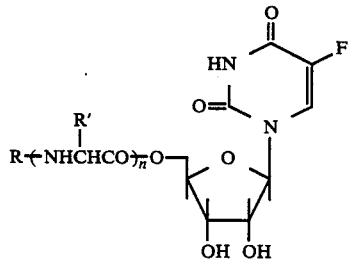

wherein n is an integer of 1 to 3, R' stands for a straight or branched chain alkyl group having 1 to 4 carbon atoms or a benzyl group, and R stands for an amino acid residue selected from the group consisting of alanyl, phenylalanyl, valyl, tyrosyl, 3,4-dihydroxyphenylalanyl and lysyl groups. These compounds possess excellent anti-malignant tumor, anti-viral and immunosuppressive activities.

24 Claims, No Drawings

OLIGOPEPTIDYL-5-FLUOROURIDINE COMPOUNDS AND PROCESS FOR PREPARING THE SAME

TECHNICAL FIELD

This invention relates to new 5-fluorouridine compounds useful as anti-malignant tumor agents, anti-viral agents or immunosuppressive agents and a process for the preparation thereof.

BACKGROUND ART

5-Fluorouridine is a compound first synthesized in 1959 (U.S. Pat. No. 2,885,396) know to have anti-malignant tumor activity. Despite its superb anti-malignant tumor activity, 5-fluorouridine has not been put to use in practice because of the disadvantage that strong side effects follow. A number of attempts to overcome such disadvantage by converting 5-fluorouridine into different derivatives (see, for example, Japanese Laid-open Patent Applns. Nos. 64280/75, 82079/75, 83378/75 and 52183/76) have been made, but useful compounds have not been obtained yet.

Although the present inventors have previously provided new 5-fluorouridine-5'-O-acyl compounds (Japanese Laid-open Patent Applns. Nos. 77298/81, 91996/82 and 91997/82), even these 5'-O-acyl compounds do not possess satisfactory properties from the practical point of view.

DISCLOSURE OF THE INVENTION

The present invention relates to new 5'-O-oligopeptidyl-5-fluorouridine compounds of the general formula:

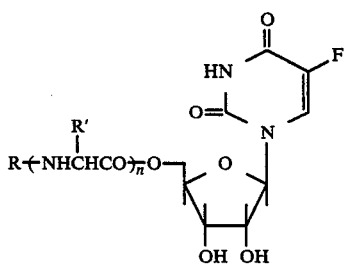

(I)

wherein n is an integer of 1 to 3, R' stands for a straight or branched chain alkyl group having 1 to 4 carbon atoms or a benzyl group, and R stands for an alanyl, phenylalanyl, valyl, tyrosyl, 3,4-dihydroxyphenylalanyl or lysyl group, and pharmacologically acceptable salts thereof, as well as a process for the preparation thereof.

The new 5'-O-oligopeptidyl-5-fluorouridine compounds of the invention and pharmacologically acceptable salts thereof have anti-malignant tumor, anti-viral and immunosuppressive activities and are therefore useful as pharmaceuticals, in particular, anti-malignant tumor agents, anti-viral agents and immunosuppressive agents.

In the 5'-O-oligopeptidyl-5-fluorouridine compounds of the general formula (I) according to the invention, the moiety represented by

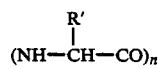

in the formula represents a peptide structure comprising 1 to 3 amino acids linked through peptide bond and selected from alanine, valine, leucine, isoleucine and phenylalanine.

Illustrative of the pharmacologically acceptable salts of these compounds are salts with mineral acids such as hydrochloric acid, nitric acid and sulfuric acid, or with organic acids such as methanesulfonic acid and para-toluenesulfonic acid.

In the following will now be described a process for the preparation of the 5'-O-oligopeptidyl-5-fluorouridine compounds mentioned above.

The 5'-O-oligopeptidyl-5-fluorouridine compounds of the invention are obtainable by N-acylating a 5'-O-acyl-5-fluorouridine or 5'-O-oligopeptidyl-5-fluorouridine derivative of the general formula:

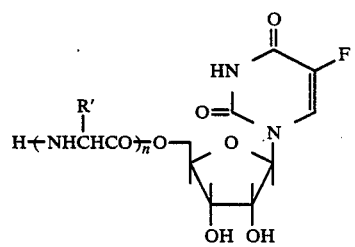

wherein n is an integer of 1 to 3, R' stands for a straight or branched chain alkyl group having 1 to 4 carbon atoms or a benzyl group, with an amino acid selected from the group consisting of alanine, phenylalanine, valine, tyrosine and 3,4-dihydroxyphenylalanine, or an acid anhydride thereof.

This reaction is carried out in a solvent in the presence of a condensing agent and a basic substance. Illustrative of the solvent are dimethylformamide, dimethylacetamide, methanol, ethanol, isopropanol, tetrahydrofuran, dioxane, acetonitrile and pyridine. Illustrative of the condensing agent are diethyl cyanophosphate, dicyclohexylcarbodiimide, p-toluenesulfonyl chloride and methane sulfonyl chloride. Illustrative of the basic substance are triethylamine, tributylamine, pyridine and lutidine. The reaction is carried out usually at room temperature using an equimolar proportion of the reactants. After the reaction, the resultant product is purified by way of column chromatography or recrystallization. The above mentioned pharmacologically acceptable salts may be formed by allowing a pharmacologically acceptable acid to be present in steps for removal of different protecting groups mentioned below, although they may be converted, after purification, into other salts.

In the reaction mentioned above, undesired reactions frequently take place. In order to prevent this, it is advisable to introduce protecting groups into either one or both of the starting materials and splitting them off after the reaction.

In one of the starting materials, i.e. a 5'-O-acyl-5-fluorouridine or 5'-O-oligopeptidyl-5-fluorouridine derivative, such undesired reaction is prone to take place at 2'- and 3'-hydroxyl groups. These 2'- and 3'-hydroxyl groups may be protected, for example, with isopropylidene, ethoxyethylidene or the like alkylidene group or benzylidene group. The other starting material amino acid requires protection because the amino group causes undesired reaction. Illustrative of the amino-protecting group are t-butoxycarbonyl, trichloroethoxycarbonyl and benzyloxycarbonyl groups and benzyloxycarbonyl groups having one or two substituents such as methoxy, methyl and nitro.

These protecting groups can be easily split off, after the reaction, in any conventional manner appropriate for the purpose. For example, the 2'- and 3'-hydroxy-protecting groups can be split off by treatment with an acid or reduction, and the amino-protecting group by reduction.

Protection of the hydroxyl groups at the 2' and 3'positions of the 5'-O-acyl-5-fluorouridine or 5'-O-oligopeptidyl-5-fluorouridine derivative may not be necessary depending upon the kind of condensing agent used in the N-acylation reaction.

The 5'-O-acyl-5-fluorouridine derivative, one of the starting materials, is a known compound, and processes for preparing the same are also known (Japanese Laid-open Patent Applns. No. 77298/81, 91996/82 and 91997/82).

The new 5'-O-oligopeptidyl-5-fluorouridine compounds possess a distinguished anti-malignant tumor activity.

In Tables 1, 2 and 3 shown below are given results in terms of percent increase in life span obtained when some compounds from several Examples described below are administered to $CDF_1$ mice inoculated with mouse leukemia cells (L-1210) and the average length of survival is compared with that for a control group.

The test procedure is as follows.

Using a group consisting of six $CDF_1$ mice $1 \times 10^5$ tumor cells of the lymphatic leukemia L-1210 (NIH strain) were inoculated intraperitoneally to the individual mice. The mice received intraperitoneal administration of a suspension of Tween-80 in physiological saline containing a test compound in an amount shown in Tables 1, 2 and 3, once a day and three times in all, i.e., on the first, fifth and ninth day from the inoculation. Percent increase in life span was calculated according to the following equation:

$$\text{Increase in Life Span (\%)} = \frac{T - C}{C} \times 100$$

T: An average of the number of survival days of the group of mice treated with the test compound C: An average of the number of survival days of the group of mice not treated with the test compound

TABLE 1

| Test Compound | Percent Increase in Life Span (1) | | | | |
|---|---|---|---|---|---|
| (Example No.) | Dose.(mg/kg) | | | | |
| | 5 | 10 | 60 | 80 | 100 |
| Compound from Example 1 | 26 | 37 | 121 | 60 | 58 |
| Compound from Example 2 | 34 | 40 | 135 | 81 | 78 |

TABLE 2

| Test Compound | Percent Increase in Life Span (2) | | | | | | |
|---|---|---|---|---|---|---|---|
| | Dose (mg/kg) | | | | | | |
| | 2.5 | 5 | 10 | 20 | 50 | 75 | 100 |
| Compound from Example 6 | 8 | 24 | 38 | 44 | 98 | 134 | 140 |

TABLE 3

| Test Compound | Percent Increase in Life Span (3) | | | | | | |
|---|---|---|---|---|---|---|---|
| | Dose (mg/kg) | | | | | | |
| | 3.13 | 6.25 | 12.5 | 25 | 50 | 75 | 100 |
| Compound from Example 7 | — | 60 | 114 (1/6) | 179 (2/6) | 173 (2/6) | — | 96 (1/6) |
| Compound from Example 11 | 17 | 20 | — | — | 74 | 160 (2/6) | 173 (2/6) |

Note:
Calculated as 30 days where the animal survived 30 days or longer.

THE EXAMPLES

EXAMPLE 1

5'-O-(N-tyrosylisoleucyl)-5-fluorouridine hydrochloride 4.0 Grams (8.90 mmol) of 5'-O-isoleucyl-2',3'-O-isopropylidene-5-fluorouridine hydrochloride was dissolved in dimethylformamide (50 ml), and 3.30 g (18 mmol) of diethylphosphoryl cyanide was then added thereto. To this solution was added dropwise under ice-cooling a solution of 8.20 g (18 mmol) of N,O-dibenzyloxycarbonyltyrosine and 3.7 g (36 mmol) of triethylamine in dimethylformamide (50 ml) over 30 minutes. The mixture was allowed to stand overnight at room temperature and concentrated under reduced pressure, and the residue was dissolved in chloroform (200 ml) and washed with 1.5% sodium hydrogen carbonate (50 ml×3). The organic layer was dried (over $Na_2SO_4$) and concentrated under reduced pressure, and the residue was subjected to separation by way of silica gel column chromatography (a linear gradient of chloroform containing 0→5% methanol), followed by concentration under reduced pressure. The residue was dissolved in 90% trifluoroacetic acid (50 ml) and the solution was stirred for 20 minutes at room temperature. The reaction liquid was concentrated and the residue was subjected to separation/purification by way of silica gel column chromatography (a linear gradient of ethyl acetate-n-hexane (1:1) containing 0→7% methanol) whereby 1.90 g (26%) of 5'-O-{N-(N,O-dibenzyloxycarbonyltyrosyl)isoleucyl-5-fluorouridine was obtained as a colorless powdery solid.

$^1$H-NMR ($CD_3OD$, TMS):δppm, 0.9 (methyl protons), 5.8 (1H, bs, $H_1'$), 6.53 (s, aromatic protons), 7.79 {1H, d(J=6.6 Hz), $H_6$}.

Elementary analysis (as $C_{40}H_{43}N_4O_{13}F.O.H_2O$):

| | C | H | N |
|---|---|---|---|
| Found (%) | 58.89 | 5.59 | 6.86 |
| Calcd. (%) | 59.15 | 5.41 | 6.90 |

1.90 Grams (2.37 mmol) of the ester obtained as described above was dissolved in ethanol (300 ml), and 0.30 g of 10% palladium-carbon and 0.75 g (7.39 mmol) of 36% hydrogen chloride-ethanol were added. The mixture was stirred in a stream of hydrogen under normal pressure for 4 hours at room temperature. The catalyst was filtered off and the filtrate was concentrated under reduced pressure. To the residue was added ethyl ether to form precipitates which were then separated by filtration to obtain 1.32 g (quantitative) of the desired 5'-O-(N-tyrosylisoleucyl)-5-fluorouridine hydrochloride as a colorless powdery solid.

$^1$H-NMR ($CD_3OD$, TMS): δ ppm, 0.9 (methyl protons), 5.8 (1H, bs, $H_1'$), 6.75 {2H, d (J=8.79 Hz), aromatic protons}, 7.10 {2H, d (J=8.54 Hz), aromatic protons}, 7.82 {1H, d (J=6.59 Hz), H$_6$}.

Elementary analysis (as C$_{40}$H$_{43}$N$_4$O$_9$F.HCl.1.2-H$_2$O.0.2C$_2$H$_5$OH)

|  | C | H | N |
|---|---|---|---|
| Found (%) | 48.54 | 6.20 | 9.04 |
| Calcd. (%) | 48.37 | 5.92 | 9.25 |

EXAMPLE 2

5'-O-(N-Lysylisoleucyl)-5-fluorouridine dihydrochloride 1.00 Gram (2.42 mmol) of 5'-O-isoleucyl-5-fluorouridine hydrochloride was dissolved in dimethylformamide (20 ml), and 1.00 g (2.85 mmol) of N$^α$,N$^ε$-di-benzyloxycarbonyllysine and 0.67 g (3.69 mmol) of diethylphosphoryl cyanide were then added. To this solution was added under ice-cooling 1.54 g (15.2 mmol) of triethylamine, and the mixture was stirred overnight at room temperature. After addition of ice water the reaction liquid was extracted with chloroform (200 ml). The organic layer was dried (over Na$_2$SO$_4$) and concentrated under reduced pressure, and the residue was subjected to separation/purification by way of silica gel column chromatography (first time: 2.5×11 cm, chloroform containing 4% methanol; second time: 5×14 cm, a linear gradient of ethyl acetate-n-hexane (1:1) containing 0→6% methanol) whereby 0.46 g (26%) of 5'-O-{N-(N$^α$,N$^ε$-di-benzyloxycarbonyllysyl)isoleucyl}-5-fluorouridine was obtained as a colorless powdery solid.

$^1$H-NMR (CD$_3$OD, TMS): δ ppm, 0.9 (methyl protons), 5.01 (s, methylene protons), 5.79 (1H, bs, H$_1$'), 7.29 (phenyl protons), 7.80 (1H, d, H$_6$)

Elementary analysis (as C$_{37}$H$_{46}$N$_5$O$_{12}$F):

|  | C | H | N |
|---|---|---|---|
| Found (%) | 57.56 | 6.21 | 8.99 |
| Calcd. (%) | 57.58 | 6.01 | 9.07 |

3.00 Grams (3.88 mmol) of the ester obtained as described above was dissolved in methanol (100 ml), and 1.20 g of 10% palladium-carbon and 0.80 g (7.70 mmol) of 36% hydrogen chloride-methanol were added. The mixture was stirred in a stream of hydrogen under normal pressure for 3 hours at room temperature. The catalyst was filtered off and the filtrate was concentrated under reduced pressure. The residue was dissolved in a small volume of ethanol, and ethyl ether was added thereto to precipitate 2.08 g (93%) of the desired 5'-O-(N-lysylisoleucyl)-5-fluorouridine dihydrochloride as a colorless powdery solid.

$^1$H-NMR (CD$_3$OD, TMS): 67 ppm, 1.0 (methyl), 3.0 (2H, t, methylene), 5.84 (1H, bs, H$_1$'), 7.90 {1H, d (J=6.47 Hz), H$_6$}. Elementary analysis (as C$_{21}$H$_{34}$N$_5$O$_8$F.2HCl.1.90H$_2$O):

|  | C | H | N |
|---|---|---|---|
| Found (%) | 41.49 | 6.77 | 11.44 |
| Calcd. (%) | 41.30 | 6.57 | 11.47 |

EXAMPLE 3

5'-O-(N-valylalanyl)-5-fluorouridine hydrochloride 1.30 Grams (2.78 mmol) of 5'-O-(N-benzyloxycarbonylalanyl)-5-fluorouridine was dissolved in ethanol (50 ml), and 0.20 g of 10% palladium-carbon and 1.00 g (9.87 mmol) of 36% hydrogen chloride-ethanol were added. The mixture was stirred in a stream of hydrogen under normal pressure for 6 hours at room temperature. The catalyst was filtered off and the filtrate was concentrated under reduced pressure whereby 1.00 g (quantitative) of 5'-O-alanyl-5-fluorouridine hydrochloride was obtained as a colorless powdery solid.

$^1$H-NMR CD$_3$OD, TMS) : δ ppm, 1.60 {3H, d (J=7.32 Hz), methyl protons}, 5.76 {1H, bd (J=3.54 Hz), H$_1$'}, 7.85 {1H, d (J=6.59 Hz), H$_6$}.

1.00 Gram (2.70 mmol) of the ester obtained as described above was dissolved in dimethylformamide (30 ml), and 0.80 g (3.20 mmol) of N-benzyloxycarbonylvaline and 0.63 g (3.86 mmol) of diethylphosphoryl cyanide were then added. To this solution was added under ice-cooling 2.70 g (26.7 mmol) of triethylamine, and the mixture was stirred for 4 hours at room temperature. The mixture was allowed to stand overnight at 4° C. and then concentrated under reduced pressure. The residue was subjected to separation/purification by way of silica gel chromatography (3×20 cm; a linear gradient of chloroform containing 3%→6% methanol) whereby 0.70 g (45.7%) of 5'-O-{N-(N-benzyloxycarbonylvalyl)alanyl}-5-fluorouridine was obtained as a colorless powdery solid.

$^1$N-NMR (CD$_3$OD, TMS): δ ppm, 1.40 {3H, d (J=7.32 Hz), methyl protons}, 5.08 (2H, s, methylene protons), 5.79 {1H, bd (J=3.54 Hz), H$_1$'}, 7.31 {5H, s, phenyl protons}, 7.85 {1H, d (J=6.59 Hz), H$_6$}.

Elementary analysis (as C$_{25}$H$_{31}$N$_4$O$_{10}$F.0.2CHCl$_3$):

|  | C | H | N |
|---|---|---|---|
| Found (%) | 51.39 | 5.53 | 9.61 |
| Calcd. (%) | 51.49 | 5.35 | 9.53 |

0.60 Gram (1.06 mmol) of the ester obtained as described above was dissolved in methanol (50 ml), and 0.20 g of 10% palladium-carbon and 0.50 g (4.94 mmol) of 36% hydrogen chloride-ethanol were added. The mixture was stirred overnight in a stream of hydrogen under normal pressure at room temperature. The catalyst was filtered off and the filtrate was concentrated under reduced pressure whereby 0.60 g (quantitative) of the desired 5'-O-(N-valylalanyl)-5-fluorouridine hydrochloride was obtained as a white powdery solid.

$^1$H-NMR (CD$_3$OD, TMS): δ ppm, 1.08 {d(J=6.83 Hz), methyl protons}, 1.10 {d (J=6.84 Hz), methyl protons}, 1.47 {d (J=7.32 Hz), methyl protons}, 5.79 (1H, bd, H$_1$'), 7.88 {1H, d (J=6.71 Hz), H$_6$}.

Elementary analysis (as C$_{17}$H$_{25}$N$_4$O$_8$F.HCl.0.2-H$_2$O.1.2C$_2$H$_5$OH)

|  | C | H | N |
|---|---|---|---|
| Found (%) | 43.98 | 6.43 | 10.38 |
| Calcd. (%) | 44.15 | 6.42 | 10.62 |

EXAMPLE 4

5'-O-(N-alanylisoleucyl)-5-fluorouridine hydrochloride 2.00 Grams (3.93 mmol) of 5'-O-(N-benzyloxycarbonylisoleucyl)-5-fluorouridine was dissolved in ethanol (80 ml), and 0.90 g of 10% palladium-carbon and 0.90 g (8.87 mmol) of 36% hydrogen chloride-ethanol were added. The mixture was stirred in a stream of hydrogen under normal pressure for 2 hours at room temperature. The catalyst was filtered off and the filtrate was concentrated under reduced pressure. The residue was dissolved in dimethylformamide (30 ml) and 1.00 g (4.48 mmol) of N-benzyloxycarbonylalanine and 0.80 g (4.90 mmol) of diethylphosphoryl cyanide were then added. To this solution was added dropwise under ice-cooling a solution of 1.20 g (11.9 mmol) of triethylamine in dimethylformamide (10 ml), and the reaction liquid was stirred for 2 hours at room temperature and then concentrated under reduced pressure. The residue was dissolved in chloroform (150 ml) and the solution was washed with a 3% aqueous solution of sodium hydrogen carbonate (100 ml). The organic layer was dried (over $Na_2SO_4$) and concentrated under reduced pressure. The residue was subjected to separation/purification by way of silica gel column chromatography (5×25 cm; chloroform solutions containing 3%, 4% and 5% methanol) whereby 0.7 g (30.7%) of 5'-O-{N-(N-benzyloxycarbonylalanyl)isoleucyl}-5-fluorouridine as a colorless powdery solid.

$^1$H-NMR ($CD_3OD$, TMS): δ ppm, 0.9 (methyl protons), 1.33 {d (J=7.08 Hz), methyl protons}, 5.08 (2H, s, methyl protons), 5.77 {1H, d (J=3.90 Hz), $H_1'$}, 7.32 (5H, s, phenyl protons), 7.82 {1H, d (J=6.59 Hz), $H_6$}.

0.79 Gram (3.10 mmol) of the ester obtained as described above was dissolved in methanol (50 ml), and 0.35 g of 10% palladium-carbon and 0.20 g (1.90 mmol) of 36% hydrogen chloride-ethanol solution were added. The mixture was stirred in a stream of hydrogen under normal pressure at room temperature. The catalyst was filtered off and the filtrate was concentrated under reduced pressure whereby 0.46 g (79.4%) of the desired 5'-O-(N-alanylisoleucyl)-5-fluorouridine hydrochloride was obtained as a colorless powdery solid.

$^1$H-NMR ($CD_3OD$, TMS): δ ppm, 1.53 {d (J=7.08 Hz), methyl protons}, 5.81 (1H, bs, $H_1'$), 7.86 {1H, d (J=6.59 Hz), $H_6$}.

EXAMPLE 5

5'-O-(N-phenylalanylisoleucyl)-5-fluorouridine hydrochloride 3.60 Grams (7.70 mmol) of 5'-O-(N-benzyloxycarbonylisoleucyl)-5-fluorouridine was dissolved in methanol (80 ml), and 0.36 g of 10% palladium-carbon and 1.00 g (9.86 mmol) of 36% hydrogen chloride-ethanol were added. The mixture was stirred overnight in a stream of hydrogen under normal pressure at room temperature. The catalyst was filtered off and the filtrate was concentrated under reduced pressure. The residue was dissolved in dimethylformamide (30 ml), and 2.41 g (8.48 mmol) of N-benzyloxycarbonylphenylalanine and 1.61 g (9.90 mmol) of diethylphosphoryl cyanide were then added. To this solution was added dropwise under ice-cooling 2.60 g (25.2 mmol) of triethylamine, and the reaction liquid was stirred for 1 hour at room temperature and concentrated under reduced pressure. The residue was dissolved in chloroform (300 ml) and pyridine (50 ml) and washed with a 3% aqueous solution of potassium hydrogen carbonate (200 ml). The organic layer was dried (over $Na_2SO_4$) and concentrated under reduced pressure, and the residue was subjected to separation/purification by way of silica gel column chromatography (a linear gradient of chloroform containing 0→6% methanol) whereby 3.10 g (68%) of 5'-O-{N-(N-benzyloxycarbonyl-phenylalanyl)isoleucyl}-5-fluorouridine was obtained as a colorless powdery solid.

$^1$H-NMR ($CD_3OD$, TMS): δ ppm, 5.00 (2H, s, methylene protons), 5.73 (1H, bs, $H_1'$), 7.21 (phenyl protons), 7.26 (phenyl protons), 7.80 {1H, d (J=6.59 Hz), $H_6$}.

3.00 Grams (4.67 mmol) of the ester obtained as described above was dissolved in methanol (100 ml), and 0.30 g of 10% palladium-carbon and 1.00 g (9.86 mmol) of 36% hydrogen chloride-ethanol were added. The mixture was stirred in a stream of hydrogen under normal pressure for 1 hour at room temperature. The catalyst was filtered off and the filtrate was concentrated under reduced pressure whereby 2.50 g (97.8%) of the desired 5'-O-{N-(phenylalanyl)isoleucyl}-5-fluorouridine hydrochloride was obtained as a colorless powdery solid.

$^1$H-NMR ($CD_3OD$, TMS): δ ppm, 0.9 (methyl protons), 5.78 (1H, d-d, $H_1'$), 7.31 (5H, s, phenyl protons), 7.81 {1H, d (J=5.69 Hz), $H_6$}.

EXAMPLE 6

5'-O-{N-(3,4-di-hydroxyphenylalanyl)isoleucyl}-5-fluorouridine hydrochloride 4.0 Grams (8.90 mmol) of 5'-O-isoleucyl- 2',3'-O-isopropylidene-5-fluorouridine hydrochloride was dissolved and 3.30 g (18 mmol) of diethylphosphoryl cyanide was then added. To this solution was added dropwise under ice-cooling over 30 minutes a solution of 11.0 g (18 mmol) of N,O,O-tribenzyloxycarbonyl-3,4-di-hydroxyphenylalanine and 3.70 g (36 mmol) of triethylamine in dimethylformamide (50 ml). The mixture was allowed to stand overnight at room temperature and concentrated under reduced pressure. The residue was dissolved in chloroform (200 ml) and the solution was washed with 1.5% sodium hydrogen carbonate (50 ml×3). The organic layer was dried (over $Na_2SO_4$) and concentrated under reduced pressure and the residue was separated by way of silica gel column chromatography (a linear gradient of chloroform containing 0→5% methanol). This residue was dissolved in 90% trifluoroacetic acid (50 ml) and the solution was stirred for 20 minutes at room temperature. The reaction liquid was concentrated under reduced pressure and the residue was subjected to separation/purification by way of silica gel column chromatography (a linear gradient of ethyl acetate-n-hexane (1:1) containing 0→7% methanol) whereby 2.0 g (23%) of 5'-0 {N-(N,O,O-tri-benzyloxycarbonyl-3,4-dihydroxyphenylalanyl)isoleucyl-5-fluorouridine was obtained as a colorless powdery solid.

$^1$H-NMR ($CD_3OD$, TMS): δ ppm, 0.9 (methyl protons), 5.01 (2H, s, methylene protons), 5.17, 5.18 (4H, s, s, methylene protons), 5.73 (1H, bd, $H_1'$), 7.27, 7.34 (s, s, phenyl protons), 7.79 {1H, d (J=5.59 Hz), $H_6$}.

Elementary analysis (as $C_{48}H_{49}N_4O_{16}F \cdot H_2O$)

|  | C | H | N |
|---|---|---|---|
| Found (%) | 59.43 | 5.48 | 5.78 |
| Calcd. (%) | 59.13 | 5.27 | 5.75 |

0.60 Gram (0.62 mmol) of the ester obtained as described above was dissolved in ethanol (50 ml), and 0.12 g of 10% palladium-carbon and 1.00 g (9.80 mmol) of 36% hydrogen chloride-ethanol were added. The mixture was stirred in a stream of hydrogen under normal pressure for 1.5 hours at room temperature. The catalyst was filtered off and the filtrate was concentrated under reduced pressure. Ethyl ether was added to the residue to form precipitates, which were then separated by filtration to obtain 0.21 g (56.6%) of 5'-O-{N-(3,4-dihydroxyphenylalanyl)isoleucyl}-5-fluorouridine monohydrochloride as a colorless powdery solid.

$^1$H-NMR (CD$_3$OD, TMS): δ ppm, 0.9 (methyl protons), 5.78 (1H, bd, H$_1$'), 6.5–7.0 (aromatic ring protons), 7.82 {1H, d (J=5.61 Hz), H$_6$}.

Elementary analysis (as C$_{24}$H$_{31}$N$_4$O$_{10}$F·HCl·2.5-H$_2$O):

|  | C | H | N |
|---|---|---|---|
| Found (%) | 45.43 | 5.56 | 8.84 |
| Calcd. (%) | 45.32 | 5.86 | 8.80 |

EXAMPLE 7

5'-O-{N-(N-lysylvalyl)alanyl}-5-fluorouridine dihydrochloride 0.6 Gram of 5'-O-(N-valylalanyl)-5-flurouridine hydrochloride obtained in Example 3 was dissolved in dimethylformamide (10 ml), and 0.40 g (1 mmol) of N$^α$,N$^ε$-di-benzyloxycarbonyllysine and 0.17 g (1 mmol) of diethylphosphoryl cyanide were then added. To this solution was added under ice-cooling 0.30 g (3 mmol) of triethylamine, and the mixture was stirred for 20 minutes. The reaction liquid was concentrated under reduced pressure and the residue was dissolved in chloroform (120 ml) and the solution was washed with 4% potassium hydrogen carbonate (50 ml). The organic layer was dried (over Na$_2$SO$_4$) and concentrated under reduced pressure, and the residue was subjected to separation/purification by way of silica gel chromatography (a linear gradient of chloroform containing 3%→6% methanol) whereby 0.50 g (49% based on 5'-O-{N-(N-benzyloxycarbonylvalyl)alanyl}-5-fluorouridine) of 5'-O-[N-{N-(N$^α$,N$^ε$-di-benzyloxycarbonyllysyl)valyl}-alanyl]-5-fluorouridine was obtained as a colorless powdery solid.

$^1$H-NMR (CD$_3$OD, TMS): δ ppm, 0.92 {d (J=6.47 Hz), methyl protons}, 0.97 {d (J=6.71 Hz), methyl protons}, 1.38 {d (J=7.32 Hz), methyl protons}, 3.10 (2H, bt, methylene protons), 5.05, 5.07 (4H, s, s, methylene protons), 5.78 {1H, bd (J=3.42 Hz), H$_1$'}, 7.30 (10H, s, phenyl protons), 7.84 ($^1$H, d (J=6.71 Hz), H$_6$}.

0.45 Gram (0.54 mmol) of the ester obtained as described above was methanol (100 ml), and 0.10 g (1 mmol) of 36% hydrogen chloride-ethanol was added. The mixture was stirred overnight in a stream of hydrogen under normal pressure at room temperature. The catalyst was filtered off and the filtrate was concentrated under reduced pressure. The residue was dissolved in a small volume of methanol, and ethyl ether was added to the solution to precipitate 0.33 g (95%) of the desired 5'-O-{N-(N-lysylvalyl)alanyl}-5-fluorouridine dihydrochloride as a colorless powdery solid.

$^1$H-NMR (CD$_3$OD, TMS) : δ ppm, 1.04 {6H, d (J=6.35 Hz), methyl protons}, 1.45 {d (J=6.59 Hz), methyl protons}, 3.00 (2H, bt, methylene protons , 5.81 (1H, bs, H$_1$'), 7.92 {1H, d (J=5.86 Hz), H$_6$}.

Elementary analysis (as C$_{23}$H$_{37}$N$_6$O$_9$F·2HCl·2-H$_2$O·0.8C$_2$H$_5$OH):

|  | C | H | N |
|---|---|---|---|
| Found (%) | 42.08 | 6.77 | 11.84 |
| Calcd. (%) | 41.82 | 6.82 | 11.90 |

EXAMPLE 8

5'-O-{N-(N-lysylalanyl)isoleucyl}-5-fluorouridine dihydrochloride 0.46 Gram of 5'-O-(N-alanylisoleucyl)-5-fluorouridine hydrochloride obtained in Example 4 was dissolved in dimethylformamide (30 ml), and 1.42 g (3.42 mmol) of N$^α$,N$^ε$-di-benzyloxycarbonyllysine and 0.90 g (5.52 mmol) of diethylphosphoryl cyanide were then added. To this solution was added under ice-cooling a solution of 1.30 g (12.9 mmol) of triethylamine in dimethylformamide, and the mixture was stirred for 1 hour at room temperature, allowed to stand overnight at room temperature and concentrated under reduced pressure. The residue was subjected to separation/purification by way of silica gel column chromatography (5×20 cm; a linear gradient of chloroform containing 3%→6% methanol) whereby 1.20 g (45.9%) of 5'-O-[N-{N-(N$^α$,N$^ε$-di benzyloxycarbonyllysyl)alanyl}isoleucyl]-5-fluorouridine was obtained as a colorless powdery solid.

$^1$H-NMR (CD$_3$OD, TMS): δ ppm, 0.9 (methyl protons), 5.05, 5.08 (4H, s, s, methylene protons), 5.76 (1H, bs, H$_1$'), 7.31 (10H, s, phenyl protons), 7.84 {1H, d (J=6.59 Hz), H$_6$}. Elementary analysis (as C$_{40}$H$_{51}$N$_6$O$_{13}$F·0.2H$_2$O):

|  | C | H | N |
|---|---|---|---|
| Found (%) | 56.49 | 6.20 | 9.95 |
| Calcd. (%) | 56.75 | 6.12 | 9.93 |

0.94 Gram (1.11 mmol) of the ester obtained as described above was dissolved in ethanol (100 ml) and methanol (20 ml), and 0.40 g of 10% palladium-carbon and 0.50 g (4.93 mmol) of 36% hydrogen chloride-ethanol were added. The mixture was stirred in a stream of hydrogen under normal pressure for 2 hours at room temperature. The catalyst was filtered off and the filtrate was concentrated under reduced pressure. The residue was washed with ether (20 ml) to obtain 0.71 g (99%) of the desired 5'-O-{N-(N-lysylalanyl)isoleucyl}-5-fluorouridine dihydrochloride as a colorless powdery solid.

$^1$H-NMR (CD$_3$OD, TMS): δ ppm, 1.41 {d (J=6.96 Hz), methyl protons}, 2.97 (t, methylene protons), 5.79 (1H, bd, H$_1$'), 7.89 {1H, d (J=6.46 Hz), H$_6$}.

Elementary analysis (as C$_{24}$H$_{39}$N$_6$O$_9$F·2HCl·H$_2$O·0.3C$_2$H$_5$OH):

|  | C | H | N |
|---|---|---|---|
| Found (%) | 43.20 | 6.71 | 12.04 |
| Calcd. (%) | 43.49 | 6.65 | 12.37 |

EXAMPLE 9

5'-O-{N-(N-alanylphenylalanyl)isoleucyl}-5-fluorouridine hydrochloride 2.50 Grams of 5'-O-{N-(phenylalanyl)isoleucyl}-5-fluorouridine hydrochloride obtained in Example 5 was dissolved in dimethylformamide (30 ml), and 1.25 g (5.60 mmol) of N-benzyloxycarbonylalanine and 1.07 g (6.53 mmol) of diethylphosphoryl cyanide were then added. To this solution was added dropwise under ice-cooling within 1 hour 1.70 g (16.8 mmol) of triethylamine, and the reaction liquid was stirred for 1 hour at room temperature and concentrated under reduced pressure. The residue was subjected to separation/purification by way of silica gel column chromatography (first time: a linear gradient of chloroform containing 0→6% methanol; second time: a linear gradient of chloroform containing 2%→6% methanol) whereby, 1.84 g (54%) of 5'-O-[N-{N-benzyloxycarbonylalanyl)-phenyl}-isoleucyl]-5-fluorouridine as a colorless powdery solid.

$^1$H-NMR (CD$_3$OD, TMS): δ ppm, 1.21 {d (J=7.20 Hz), methyl protons}, 5.04 (2H, s, methylene protons), 5.78 (1H, bd, H$_1$') 7.20 (5H, s, phenyl protons), 7.32 (5H, s, phenyl protons), 7.79 {1H, d (J=6.59 Hz), H$_6$}.

1.29 Grams (1.64 mmol) of the ester obtained as described above was dissolved in methanol (100 ml), and 0.20 g of 10% palladium-carbon and 0.20 g (2 mmol) of 36% hydrogen chloride-ethanol were added. The mixture was stirred in a stream of hydrogen under normal pressure for 2 hours at room temperature. The catalyst was filtered off and the filtrate was concentrated under reduced pressure to obtain 1.01 g (99%) of the desired 5'-O-{N-(N-alanylphenylalanyl)isoleucyl}-5-fluorouridine hydrochloride as a white powdery solid.

$^1$H-NMR (CD$_3$OD, TMS): δ ppm, 1.48 {d (J=7.08 Hz), methyl protons}, 5.74 (1H, bd, H$_1$'), 7.25 (5H, s, phenyl protons), 7.84 {1H, d (J=6.59 Hz), H$_6$}.

EXAMPLE 10

5'-O-{N-(N-phenylalanylalanyl)isoleucyl}-5-fluorouridine hydrochloride 0.46 Gram of 5'-O-(N-alanylisoleucyl)-5-fluorouridine hydrochloride obtained in Example 4 was dissolved in dimethylformamide (20 ml), and 1.51 g (5.30 mmol) of N-benzyloxycarbonylphenylalanine and 1.10 g (6.74 mmol) of diethylphosphoryl cyanide were then added. To this solution was added dropwise under ice-cooling a solution of 2.40 g (23.8 mmol) of triethylamine in diethylformamide (3 mmol), and the reaction liquid was kept for 17 hours at −20° C. and then concentrated under reduced pressure. The residue was dissolved in chloroform (200 ml) and the solution was washed with a 3% aqueous solution of potassium hydrogen carbonate (100 ml). The aqueous layer was further extracted with chloroform (100 ml). These organic layers were dried (over Na$_2$SO$_4$) and then concentrated under reduced pressure, and the residue was subjected to separation/purification by way of silica gel column chromatography (first time: a linear gradient of chloroform containing 3%→6% methanol; second time: a linear gradient of chloroform containing 3%→6% methanol) whereby 1.25 g (35%) of 5'-O-[N-{(N-benzyloxycarbonylphenylalanyl)alanyl}isoleucyl]-5-fluorouridine was obtained as a colorless powdery solid.

$^1$H-NMR (CD$_3$OD, TMS): δ ppm, 1.33 {d (J=6.96 Hz), methyl protons}, 5.79 {1H, d-d (J=3.78 Hz), H$_1$'}, 7.21, 7.25 (10H, s, s, phenyl protons), 7.81 {1H, d (J=6.60 Hz), H$_6$}.

Elementary analysis (as C$_{33}$H$_{42}$N$_5$O$_{11}$F.0.3CHCl$_3$):

|  | C | H | N |
|---|---|---|---|
| Found (%) | 55.79 | 5.63 | 9.30 |

-continued

|  | C | H | N |
|---|---|---|---|
| Calcd. (%) | 55.53 | 5.58 | 9.17 |

1.20 Grams (1.65 mmol) of the ester obtained as described above was dissolved in methanol (50 ml), and 0.20 g of 10% palladium-carbon and 0.30 g (2.96 mmol) of 36% hydrogen chloride-ethanol were added. The mixture was stirred in a stream of hydrogen under normal pressure for 1 hour at room temperature. The catalyst was filtered off and the filtrate was concentrated under reduced pressure to obtain 1.05 g (quantitative) of the desired 5'-O-{N-(N-phenylalanylalanyl)isoleucyl}-5-fluorouridine hydrochloride as a colorless powdery solid.

$^1$H-NMR (CD$_3$OD, TMS): δ ppm, 1.39 {d (J=7.08 Hz), methyl protons}, 5.79 {1H, d (J=3.55 Hz), H$_1$'}, 7.32 (5H, s, phenyl protons), 7.88 {1H, d (J=6.59 Hz), H$_6$}.

EXAMPLE 11

5'-O-[N-{N-(lysylalanyl)phenylalanyl}isoleucyl]-5-fluorouridine dihydrochloride 1.04 Grams (1.65 mmol) of 5'-O-{N-(N-alanylphenylalanyl)isoleucyl}-5-fluorouridine hydrochloride obtained in Example 9 was dissolved in dimethylformamide (10 ml), and 0.815 g (1.97 mmol) of N$^α$,N$^ε$-di-benzyloxycarbonyllysine and 0.375 g (2.30 mmol) of diethylphosphoryl cyanide were then added. To this solution was added under ice-cooling 0.60 g (5.90 mmol) of triethylamine, and the mixture was stirred for 1 hour at room temperature. The reaction liquid was concentrated under reduced pressure, and the residue was subjected to separation/purification by way of silica gel column chromatography (first time: a linear gradient of chloroform containing 2%→6% methanol; second time: a linear gradient of chloroform containing 3%→6% methanol) whereby 0.85 g (52.3%) of 5'-O-[N-{N-(N$^α$,N$^ε$-dibenzyloxycarbonyllysyl)alanyl}phenylalanyl]isoleucyl]-5-fluorouridine was obtained as a colorless powdery solid.

$^1$H-NMR (CD$_3$OD, TMS): δ ppm, 1.21 {d (J=7.33 Hz), methyl protons}, 5.04 (2H, s, methylene protons), 5.09 (2H, s, methylene protons), 5.78 (1H, bd, H$_1$'), 7.18 (5H, s, phenyl protons), 7.30 (10H, s, phenyl protons), 7.78 {1H, d (J=6.47 Hz), H$_6$}.

Elementary analysis (as C$_{49}$H$_{60}$N$_7$O$_4$F.H$_2$O):

|  | C | H | N |
|---|---|---|---|
| Found (%) | 58.43 | 6.12 | 9.89 |
| Calcd. (%) | 58.38 | 6.20 | 9.73 |

0.85 Gram (0.86 mmol) of the ester obtained as described above was dissolved in methanol (150 ml), and 0.20 g of 10% palladium-carbon and 0.20 g (1.97 mmol) of 36% hydrogen chloride-ethanol were added. The mixture was stirred in a stream of hydrogen under normal pressure for 3 hours at room temperature. The catalyst was filtered off and the filtrate was concentrated under reduced pressure to obtain 0.55 g (80.5%) of the desired 5'-O-[N-{N-(N-lysylalanyl)phenylalanyl}isoleucyl]-5-fluorouridine dihydrochloride as a colorless powdery solid.

$^1$H-NMR (CD$_3$OD, TMS): δ ppm, 5.74 (1H, bs, H$_1$'), 7.24 (5H, s, phenyl protons), 7.82 (1H, d, H$_6$).

Elementary analysis (as $C_{33}H_{48}N_7O_{10}F\cdot 2HCl\cdot 2.5\text{-}H_2O$)

|  | C | H | N |
|---|---|---|---|
| Found (%) | 47.45 | 6.52 | 11.38 |
| Calcd. (%) | 47.20 | 6.36 | 11.67 |

EXAMPLE 12

5'-O-[N-{N-(N-lysylphenylalanyl)alanyl isoleucyl]-5-fluorouridine dihydrochloride.

1.05 Grams of 5'-O-{N-(N-phenylalanylalanyl)isoleucyl)-5-fluorouridine}hydrochloride was dissolved in dimethylformamide (30 ml), and 0.68 g (1.64 mmol) of $N^\alpha,N^\epsilon$-di-benzyloxycarbonyllysine and 0.30 g (1.83 mmol) of diethylphosphoryl cyanide were then added. To this solution was added under ice-cooling a solution of 0.50 g (4.95 mmol) of triethylamine in dimethylformamide (1 ml), and the mixture was stirred for 1 hour at room temperature. The reaction liquid was concentrated under reduced pressure. The residue was dissolved in chloroform (200 ml) and the solution was washed with a 0.2% aqueous solution of potassium hydrogen carbonate (100 ml). The organic layer was dried (over $Na_2SO_4$) and concentrated under reduced pressure, and the residue was subjected to separation/purification by way of silica gel column chromatography(first time: a linear gradient of chloroform containing 2%→4% methanol; second time: a linear gradient of chloroform containing 3%→6% methanol) whereby 0.83 g (50%) of 5'-O-[N-[N-{N-($N^\alpha,N^{68}$-di-benzyloxycarbonyllysyl)phenylalanyl}alanyl]isoleucyl]-5-fluorouridine was obtained as a colorless powdery solid.

$^1$H-NMR (CD$_3$OD TMS): δ ppm, 1.33 {d (J=7.08 Hz), methyl protons}, 5.04 (4H, s, methylene protons), 7.19, 7.29, 7.31 (15H, s, s, s, phenyl protons), 7.78 {1H, d (J=6.35 Hz), H$_6$}.

Elementary analysis (as $C_{49}H_{60}N_7O_{14}F\cdot 0.25CHCl_3$)

|  | C | H | N |
|---|---|---|---|
| Found (%) | 57.73 | 5.81 | 9.73 |
| Calcd. (%) | 58.00 | 5.95 | 9.61 |

0.87 g (0.88 mmol) of the ester obtained as described above was dissolved in ethanol (60 ml), and 0.20 g of 10% palladium-carbon and 0.20 g (2.0 mmol) of 36% hydrogen chloride-ethanol were added. The mixture was stirred overnight in a stream of hydrogen under normal pressure at room temperature. The catalyst was filtered off and the filtrate was concentrated under reduced pressure. The residue was washed with ether to obtain 0.64 g (91%) of the desired 5'-O-[N-{ N-(N-lysyl-phenylalanyl)alanyl}isoleucyl]-5-fluorouridine dihydrochloride as a colorless powdery solid.

1H-NMR (CD$_3$OD, TMS): δ ppm, 1.37 {d (J=6.96 Hz), methyl protons}, 5.78 (bs, H$_1$'), 7.27 (s, phenyl protons), 7.87 {d (J=6.59 Hz), H$_6$}.

Elementary analysis (as $C_{33}H_{48}N_7O_{10}\cdot 2HCl\cdot 2.2H_2O\cdot 0.46C_2H_5OH$)

|  | C | H | N |
|---|---|---|---|
| Found (%) | 47.41 | 6.55 | 11.21 |
| Calcd. (%) | 47.62 | 6.73 | 11.46 |

Industrial Applicability

The new 5'-O-oligopeptidyl-5-fluorouridine compounds of the present invention possess excellent anti-malignant tumor, anti-viral and immunosuppressive activities and are therefore useful as pharmaceuticals or intermediates for the preparation thereof.

We claim:

1. 5'-O-oligopeptidyl-5-fluorouridine compounds of the general formula:

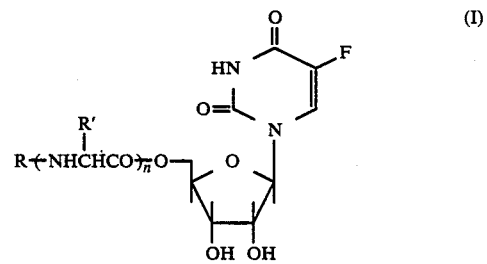

wherein n is an integer of 1 to 3, R' stands for a straight or branched chain alkyl group having 1 to 4 carbon atoms or a benzyl group, and R stands for an amino acid residue selected from the group consisting of alanyl, phenylalanyl, valyl, tyrosyl, 3,4-dihydroxyphenylalanyl and lysyl groups, or pharmacologically acceptable salts thereof.

2. 5'-O-oligopeptidyl-5-fluorouridine compounds or pharmacologically acceptable salts thereof as claimed in claim 1, wherein said group

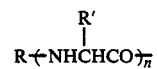

is an oligopeptidyl group selected from the group consisting of N-tyrosylisoleucyl, N-lysylisoleucyl, N-valylalanyl, N-alanylisoleucyl, N-phenylalanylisoleucyl, N-(3,4-di-hydroxyphenylalanyl)isoleucyl, N-(N-lysylvalyl)alanyl, N-(N-lysylalanyl)isoleucyl, N-(N-alanylphenylalanyl)isoleucyl, N-(N-phenylalanylalanylisoleucyl, N-(N-(lysylalanyl)-phenylalanyl)isoleucyl and N-(N-(N-lysylphenylalanyl)alanyl}isoleucyl.

3. The compounds as claimed in claim 2, wherein said 5'-O-oligopeptidyl-5-fluorouridine compounds are in the form of pharmacologically acceptable salts selected from the group consisting of salts of hydrochloric acid, nitric acid, sulfuric acid, methanesulfonic acid, and para-toluenesulfonic acid.

4. The compounds as claimed in claim 1, wherein said 5'-O-oligopeptidyl-5-fluorouridine compounds are in the form of pharmacologically acceptable salts selected from the group consisting of salts of hydrochloric acid, nitric acid, sulfuric acid, methanesulfonic acid, and para-toluenesulfonic acid.

5. A compound selected from the compounds claimed in claim 1, comprising 5'-O-(N-tyrosylisoleucyl)-5-fluorouridine or a pharmacologically acceptable salt thereof.

6. A compound selected from the compounds claimed in claim 1, comprising 5'-O-(N-Lysylisoleucyl)-5-fluorouridine or a pharmacologically acceptable salt thereof.

7. A compound selected from the compounds claimed in claim 1, comprising 5'-O-(N-valylalanyl)-5-fluorouridine or a pharmacologically acceptable salt thereof.

8. A compound selected from the compounds claimed in claim 1, comprising 5'-O-(N-alanylisoleucyl)-5-fluorouridine or a pharmacologically acceptable salt thereof.

9. A compound selected from the compounds claimed, in claim 1, comprising 5'-O-(N-phenylalanylisoleucyl)-5-fluorouridine or a pharmacologically acceptable salt thereof.

10. A compound selected from the compounds claimed, in claim 1, comprising 5'-O-{N-(3,4-di-hydroxyphenylalanyl)isoleucyl}-5-fluorouridine or a pharmacologically acceptable salt thereof.

11. A compound selected from the compounds claimed in claim 1, comprising 5'-O-{N-(N-lysylvalyl)alanyl}-5-fluorouridine or a pharmacologically acceptable salt thereof.

12. A compound selected from the compounds claimed in claim 1, comprising 5'-O-{N-(N-lysylalanyl)isoleucyl}-5-fluorouridine or a pharmacologically acceptable salt thereof.

13. A compound selected from the compounds claimed in claim 1, comprising 5'-O-{N-(N-alanylphenylalanyl)isoleucyl}-5-fluorouridine or a pharmacologically acceptable salt thereof.

14. A compound selected from the compounds claimed in claim 1, comprising 5'-O-{N-(N-phenylalanylalanyl)isoleucyl}-5-fluorouridine or a pharmacologically acceptable salt thereof.

15. A compound selected from the compounds claimed in claim 1, comprising 5'-O-[N-{N-(lysylalanyl)phenylalanyl}isoleucyl]-5-fluorouridine or a pharmacologically acceptable salt thereof.

16. A compound selected from the compounds claimed in claim 1, comprising 5'-O-[N-{N-(lysylphenylalanyl)alanyl}isoleucyl]-5-fluorouridine or a pharmacologically acceptable salt thereof.

17. A pharmaceutical composition comprising, as an active ingredient, an effective amount of a 5'-O-oligopeptidyl-5-fluorouridine compound of the general formula:

$$R \!-\!(\mathrm{NHCHCO})_{\overline{n}} \!-\! \mathrm{O} \!-\! \text{[ribose-base]} \quad (I)$$

wherein n is an integer of 1 to 3, R' stands for a straight or branched chain alkyl group having 1 to 4 carbon atoms or a benzyl group, and R stands for an amino acid resins selected from the group consisting of alanyl, phenylalanyl, valyl, tyrosyl, 3,4-dihydroxyphenylalanyl and lysyl groups, or a pharmacologically acceptable salt thereof; and a pharmaceutically acceptable excipient.

18. The composition as claimed in claim 17, wherein said group $$R \!-\!(\mathrm{NHCHCO})_{\overline{n}}$$

is an oligopeptidyl group selected from the group consisting of N-tyrosylisoleucyl, N-lysylisoleucyl, N-valylalanyl, N-alanylisoleucyl, N-phenylalanylisoleucyl, N-(3,4-di-hydroxyphenylalanyl)isoleucyl, N-(N-lysylvalyl)alanyl, N-(N-lysylalanyl)isoleucyl, N-(N-alanylphenylalanyl)isoleucyl, N-(N-phenylalanylalanylisoleucyl, N-{N-(lysylalanyl)phenylalanyl}isoleucyl and N-{N-(N-lysylphenylalanyl)alanyl}isoleucyl.

19. A method for the treatment of malignant tumors, viral infections or the immune system which comprises administering to a patient an effective amount of a compound selected from
5'-O-oligopeptidyl-5-fluorouridine compounds of the general formula:

$$R \!-\!(\mathrm{NHCHCO})_{\overline{n}} \!-\! \mathrm{O} \!-\! \text{[ribose-base]} \quad (I)$$

wherein n is an integer of 1 to 3, R' stands for a straight or branched chain alkyl group having 1 to 4 carbon atoms or a benzyl group, and R stands for an amino acid residue selected from the group consisting of alanyl, phenylalanyl, valyl, tyrosyl, 3,4-dihydroxyphenylalanyl and lysyl groups, or pharmacologically acceptable salts thereof.

20. The method of claim 19, wherein said group $$R \!-\!(\mathrm{NHCHCO})_{\overline{n}}$$

is an oligopeptidyl group selected from the group consisting of N-tyrosylisoleucyl, N-lysylisoleucyl, N-valylalanyl, N-alanylisoleucyl, N-phenylalanylisoleucyl, N(3,4-di-hydroxyphenylalanyl)isoleucyl, N-(N-lysylvalyl)alanyl, N-(N-lysylalanyl)isoleucyl, N-(N-alanylphenylalanyl)isoleucyl, N-(N-phenylalanylalanyl isoleucyl, N-{N-(lysylalanyl)phenylalanyl}isoleucyl and N-{N-(lysylphenylalanyl)alanyl}isoleucyl.

21. The method of claim 19, wherein said compound is administered to a patient so as to treat malignant tumors.

22. The method of claim 19, wherein said compound is administered to a leukemia patient so as to treat leukemia tumors.

23. The method of claim 19, wherein said compound is administered to a patient so as to treat viral infections.

24. The method of claim 19, wherein said compound is administered to a patient so as to treat the immune system.

* * * * *